United States Patent [19]
Christian

[11] Patent Number: 5,141,498
[45] Date of Patent: Aug. 25, 1992

[54] FLEXIBLE VALVE AND DEVICE INCORPORATING THE SAME

[75] Inventor: Jeffrey J. Christian, San Jose, Calif.

[73] Assignee: Unisurge, Incorporated, Palo Alto, Calif.

[21] Appl. No.: 757,343

[22] Filed: Sep. 10, 1991

[51] Int. Cl.⁵ ............................................ A61M 25/00
[52] U.S. Cl. .................................. 604/167; 251/149.1
[58] Field of Search ............................. 604/237, 167; 251/149.1; 137/849

[56] References Cited

U.S. PATENT DOCUMENTS

| | | | |
|---|---|---|---|
| 3,861,416 | 1/1975 | Wichterle | 137/849 |
| 4,143,853 | 3/1979 | Abramson | 604/237 |
| 4,177,814 | 12/1979 | Knepshield et al. | 604/167 |
| 4,222,126 | 9/1980 | Boretos et al. | 137/849 |
| 4,364,127 | 12/1982 | Pierce et al. | 137/849 |
| 4,375,864 | 3/1983 | Savage | 251/149.1 |
| 4,424,833 | 1/1984 | Spector et al. | 137/849 |
| 4,475,548 | 10/1984 | Muto | 604/167 |
| 4,673,393 | 6/1987 | Suzuki et al. | 604/167 |
| 4,765,588 | 8/1988 | Atkinson | 251/149.1 |
| 4,798,594 | 1/1989 | Hillstead | 604/167 |
| 4,809,679 | 3/1989 | Shimonaka et al. | 604/167 |

Primary Examiner—Paul J. Hirsch
Attorney, Agent, or Firm—Flehr, Hohbach, Test, Albritton & Herbert

[57] ABSTRACT

Flexible valve adpated to have a device inserted therethrough having a body of elastomeric material comprising a cylindrical wall portion with a bore extending therethrough and having a longitudinal central axis. At least three flexible leaflets are provided which adjoin the cylindrical wall portion and subtend 360° of the cylindrical wall portion and are adapted to have said device inserted therethrough. Each leaflet has inwardly inclined planar adjoining first and second wall portions and is vee-shaped in cross-section in a plane perpendicular to the central axis. Each of the first and second wall portions have first and second sealing surfaces at their distal extremities. The first and second sealing surfaces of one of the leaflets is adapted to abut the second sealing surface of the adjacent leaflet on one side of said one leaflet and abut the first edge of the adjacent leaflet on the other side of said one leaflet whereby a yieldable seal is formed by the abutting sealing surfaces of the leaflets when a device is not present in the valve.

16 Claims, 2 Drawing Sheets

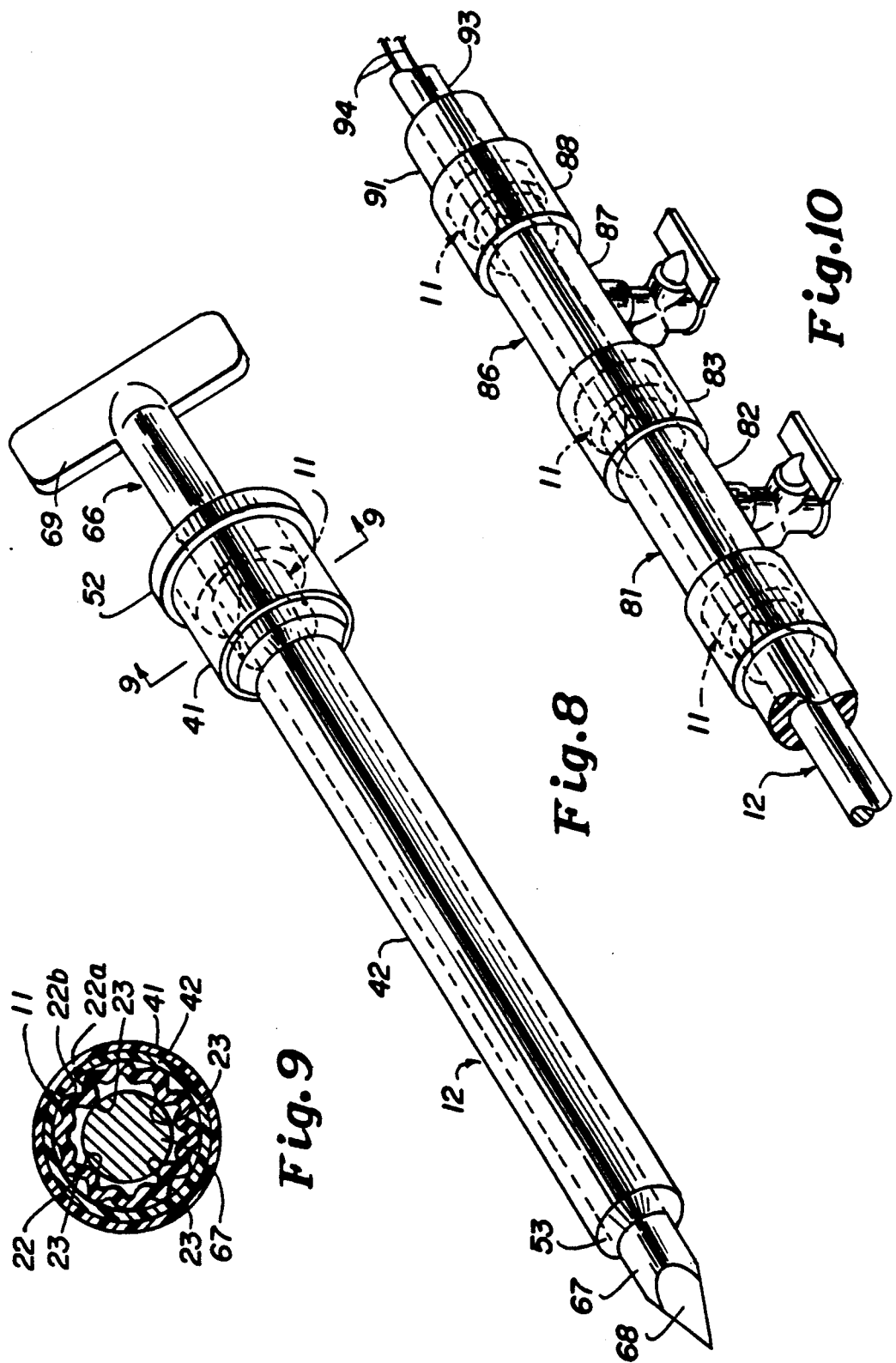

FLEXIBLE VALVE AND DEVICE INCORPORATING THE SAME

This invention relates to a flexible valve and a device incorporating the same and more particularly to a flexible valve having several leaflets and a laparoscopic device incorporating the same.

Flexible valves have heretofore been provided, however, they have typically been of what is called the "duckbill" type which are provided with two leaflets. In a number of applications such valves are found to be unsuitable particularly when relatively large diameter devices or tools are inserted and withdrawn through the same because there has been a tendency for the duckbill valves to invert when the device or tool are withdrawn from the valves. There is therefore a need for a new and improved flexible valve to overcome this disadvantage.

In general, it is an object of the present invention to provide a flexible valve and a device incorporating the same which permits sealing with respect to large diameter devices or tools inserted through the device.

Another object of the invention is to provide a flexible valve of the above character which does not invert when a tool or device is withdrawn therefrom.

Another object of the invention is to provide a flexible valve of the above character which has reduced friction on withdrawal.

Another object of the invention is to provide a flexible valve of the above character which readily seals when the tool or device is removed therefrom.

Another object of the invention is to provide a flexible valve and device incorporating the same which can be nested with other devices utilizing the same type of flexible valve.

Another object of the invention is to provide a flexible valve of the above character which provides increased sealing surfaces.

Another object of the invention is to provide a flexible valve of the above character which can be readily and economically manufactured.

Additional objects and features of the invention will appear from the following description from which the preferred embodiments are set forth in detail in conjunction with the accompanying drawings.

FIG. 8 is an isometric view showing the device in FIG. 1 being utilized with a tool in the form of a trocar.

FIG. 9 is a cross-sectional view taken along the line 9—9 of FIG. 8.

FIG. 10 is an isometric view showing an assembly of devices incorporating the present invention showing the manner in which they can be nested.

In general, the flexible valve of the present invention which is adapted to have a device inserted therethrough is comprised of a body of elastic material. The body has a cylindrical wall portion with a bore extending therethrough and has a longitudinal central axis. The body also has at least three flexible leaflets adjoining the cylindrical portion and being adapted to permit a device to be inserted therethrough. Each leaflet has an inwardly inclined planar adjoining first and second wall portions forming a vee in cross-section in a plane perpendicular to the central axis. Each of the first and second walls has first and second edges at their distal extremities. The first and second edges of one of said leaflets are adapted to abut the second edge of the leaflet adjacent one side of said one leaflet and abut the first edge of the leaflet adjacent the other side of said one leaflet whereby a seal is formed by the abutting edges of the leaflets when a device is not present in the valve.

Figure 1:
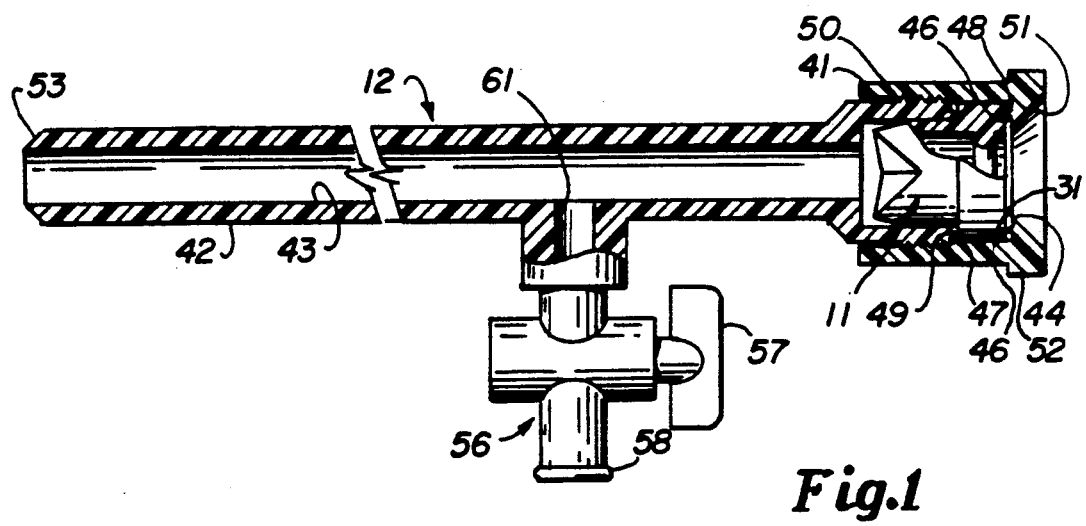
FIG. 1 is a cross-sectional view of a flexible valve incorporating the present invention and a device incorporating the flexible valve.
Figure 3:
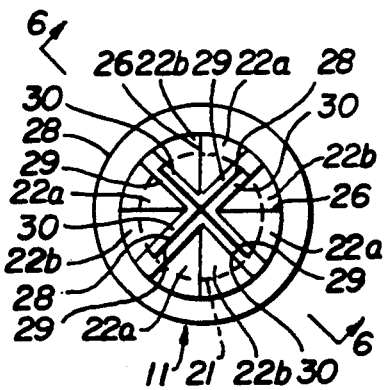
FIG. 3 is a top plan view of the valve shown in FIG. 2 looking along the line 3—3 of FIG. 2.
Figure 2:
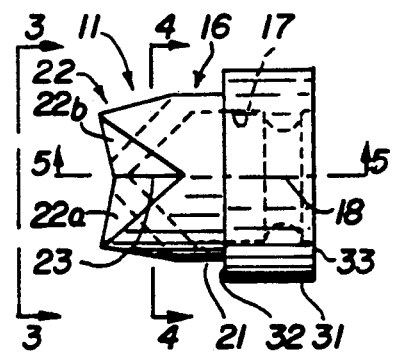
FIG. 2 is an elevational view of the flexible valve shown in FIG. 1.

More particularly, the flexible valve 11 is shown in FIGS. 1, 2 and 3 and is incorporated in a device 12 shown in FIG. 1. The flexible valve 11 is in the form of a body 16 formed of a suitable elastomeric material. Elastomeric materials which have been found to be satisfactory are urethane compounds having a Shore A hardness ranging from 20 to 50 and preferably a Shore A hardness of 35. C-Flex, trademark, manufactured by Concept Polymers Technologies, Incorporated, Clearwater, Fla., is a suitable urethane compound. A rubber-like compound identified as Krayton, trademark, manufactured by Shell Corporation, Houston, Tex., can also be used. Elastomeric materials having self-lubricating properties as, for example, those containing silicone such as supplied by General Electric and Dow Chemical can be used, also a thermoplastic elastomeric material such as Santoprene, trademark, by Monsanto Chemical of St. Louis, Mo. Latex can also be used, however, its use is not as desirable, because of the high degree of tackiness which it presents, and also because of its lack of uniformity since it is a natural material. The flexible valve 11 is formed from a body of this material by suitable means such as by injection molding or the like. The body 16 is provided with a central bore 17 extending therethrough which has a longitudinally extending central axis 18.

Figure 6:
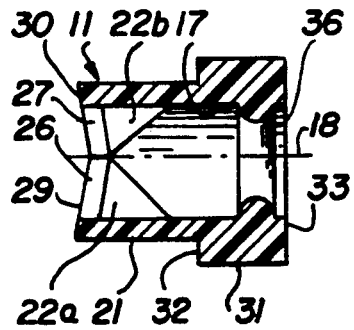
FIG. 6 is a cross-sectional view taken along the line 6—6 of FIG. 3.

The body 16 forming the flexible valve 11 is provided with a cylindrical wall portion 21 disposed coaxially of the axis 18. At least three or several leaflets 22 are provided as a part of the flexible valve 11 and as shown four of such leaflets 22 have been provided which subtend 360° of the cylindrical wall portion 21. Each leaflet 22 has inwardly inclined planar adjoining first and second wall portions 22a and 22b. Each of the leaflets 22 is vee-shaped in cross-section in a plane which is perpendicular to the central axis 18. The wall portions 22a and 22b adjoin at the apex 23 of the vee. The proximal extremities of the leaflets 22 are formed integral with the cylindrical wall portion 21, whereas the distal extremities are provided with first and second sealing surfaces 26 and 27 which lie in planes generally parallel to the axis 18. The first and second sealing surfaces 26 and 27 of one of the leaflets are adapted to yieldably abut the second sealing surface 27 of the leaflet adjacent one side of said one leaflet and yieldably abut the first sealing surface 26 of said one leaflet adjacent the other side of said one leaflet whereby elongate or linear seals 28 are formed by the yieldable abutting surfaces of the leaflets to seal off the bore 17 passing through the body 16. The distal extremities of the leaflets 22 are also formed with planar surfaces 29 and 30 adjoining the sealing surfaces 26 and 27 at an angle of approximately 90°. The planar surfaces 29 and 30 are inclined inwardly and downwardly (see FIGS. 2 and 6) as, for example, approximately 5-20° from a line extending perpendicular to the axis 18. The sealing surfaces 26 and 27 have relatively large areas so that seals are established over such large areas rather than only over a line contact. The planar abutting surfaces 29 and 30 provide seals which have bulk rather than a knife edge so that they will not readily invert during use.

Figure 5:
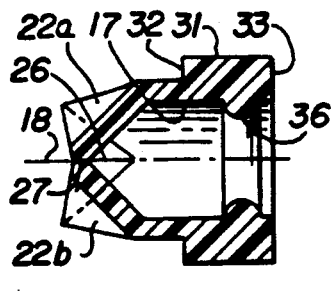
FIG. 5 is a cross-sectional view taken along the line 5—5 of FIG. 2.

The body 16 of the valve 11 is provided with an annular flange 31 through which the bore 17 extends, which is formed integral with the cylindrical wall portion 21 to provide upper and lower planar parallel surfaces 32 and 33. A seal ring 36 (see FIGS. 5 and 6) arcuate in cross-section which serves as an O-ring is formed integral with the flange 31 and circumscribes the bore 17 to form a seal as hereinafter described. The size of the O-ring is selected to accommodate the size of the tool to pass through the valve 11. Also it should be appreciated that the O-ring seal can be made so that it is very flexible to accommodate a range of sizes of tools to pass through the valve 11.

The cylindrical wall portion 21 and the leaflets 22 can have a suitable thickness as, for example, from 0.020 inches to 0.040 inches and preferably a thickness of approximately 0.030 inches. The annular flange 31 can have a suitable thickness as, for example, 0.060 inches and can have a height of approximately ¼ of an inch. The cylindrical wall portion 21 and the leaflets 22 can have a height of approximately ⅜ of an inch. The cylindrical wall portion can have a diameter of approximately ⅜ of an inch. As hereinafter described, a flexible valve 11 of this character can be utilized in connection large diameter devices as, for example, those having a diameter in the range of 10 mm, but also in a range of sizes from 3 mm to 25 mm.

The device 12 which incorporates and utilizes the flexible valve 11 mounted therein as shown in FIG. 1 is in the form of an introducer and consists of a first part 41 in the form of a cylindrical member and a second part 42 in the form of an elongate cylindrical member. The parts 41 and 42 can be formed of a suitable material such as plastic. The device 12 can be considered as a valve holder for holding the flexible valve 11. The part 42 is provided with a central bore 43 extending longitudinally therethrough and is in registration with a bore 44 provided in the part 41. The parts 41 and 42 are provided with annular planar surfaces 46 and 47 disposed on opposite sides of the flange 31 of the valve 11 and are adapted to engage the surfaces 33 and 32, respectively of the flange 31 of the valve 11. In order to provide an improved sealing engagement, the parts 41 and 42 can be provided with annular ridges 48 and 49 on the surfaces 46 and 49 which are triangular in cross-section engaging the surfaces 33 and 32. Means is provided for interconnecting the first and second parts to clamp the flange 31 of the valve ii between the surfaces 46 and 47 of the parts 41 and 42 and takes the form of a threaded connection 49 formed between the parts 41 and 42 in which mating threads are carried by each of the parts and in which the threaded connection 49 can be adjusted to apply the appropriate clamping forces to the surfaces 32 and 33 of the flange 31. It should be appreciated that a bayonet back can be substituted for the threaded connection. The part 41 is provided with a conical tapered surface 51 which adjoins the bore 44 and extends in an outwardly inclined direction. The part 41 is also provided with a radially extending flange 52. The distal extremity of the second part is provided with a rounded distal extremity 53 as shown.

A conventional stop cock 56 is mounted on the elongate cylindrical member of second part 42 and is provided with an operating knob 57 and an inlet 58. The inlet 58, when the valve stop cock 56 is in its open position, is in communication with an inlet passage 61 provided in the part 52 and is in communication with the bore 43 and is disposed below the valve 11 as shown in FIG. 1.

Figure 7:
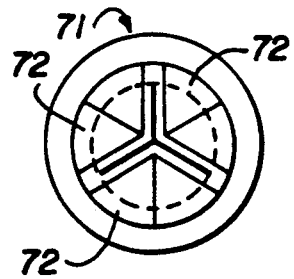
FIG. 7 is a top plan view similar to FIG. 3 of another embodiment of a flexible valve incorporating the present invention.

As shown in FIG. 7, the device 12 shown in FIG. 1 With the flexible valve 11 mounted in can be utilized as an introducer for various types of devices or tools as, for example, a trocar 66 of a conventional type. The trocar 66 is provided with a steel shaft 67 having a pointed end 68 on one end of the shaft 67 and a handle 69 on the other end of the shaft. By way of example, the introducer device 12 and the trocar 66 can be utilized in connection with endoscopic surgery as, for example, in performing operations in the abdominal cavity which has been inflated with a suitable gas as, for example, $CO_2$ and in which it is desired to make additional penetrations in the stomach wall. This can be readily accomplished by the introducer device 12 in connection with the trocar 66 to provide an additional penetration through the abdominal wall and then utilizing the introducer device 12 with the valve 11 therein to have retained the gas within the abdominal cavity by the O-ring 36 of the valve 11 engaging the shaft 67 of the trocar and forming a sealing engagement therewith.

After the puncture has been made, the trocar 66 can be readily withdrawn from the flexible valve 11 because of the minimal frictional engagement between the valve leaflets 22 and the shaft 67 of the trocar without any danger of inversion of the leaflets 22. As shown in FIG. 9 the apices 23 of the leaflets 22 only engage the shaft 67 to provide only a four-point contact for the form leaflets 22. After the trocar has been withdrawn the leaflets 22 are permitted to close on themselves to form a good seal to prevent the escape of any gases from the abdominal cavity. Thereafter, additional tools can be inserted through the introducer device 12 by inserting the same through the valve 11. The valve 11, because of its construction, provides an excellent seal around the tool while at the same time permitting ready withdrawal of the tool without any danger of inversion.

Figure 4:
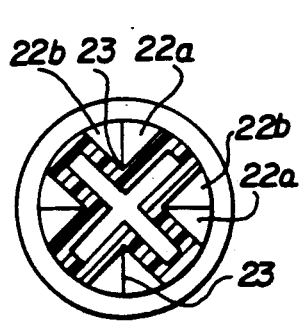
FIG. 4 is a cross-sectional view of the valve shown in FIG. 2 taken along the line 4—4 of FIG. 2.

In FIG. 7, there is shown another embodiment of a flexible valve incorporating the present invention showing that several or in other words, greater than 2 leaflets can be used for the flexible valve. Thus, there is shown in FIG. 7, a flexible valve 71 in which three leaflets 72 are provided which adjoin the cylindrical body (not shown) adjoining the flange 73. Thus, there are provided the three leaflets, each of which subtend 120° of the 360° of the flange 73, rather than the 90° subtended by the leaflets 22 of the valve 11. The leaflets 72 are constructed in the same manner as the leaflets 22 and have the same general confirmation. The valve 71 will operate in the same manner as the valve in FIGS. 2, 3 and 4 with the only difference being that three leaflets are provided rather than four. It is believed that slightly improved sealing can be obtained with the four leaflets over the three leaflets. It also should be appreciated that other flexible valves can be provided with additional leaflets as, for example, six or eight leaflets subtending the 360°. Such constructions might be particularly appropriate for larger flexible valves incorporating the present invention.

It should be appreciated that the flexible valves of the present invention can be utilized in various devices incorporating the same principles to permit nesting of the devices with one of the devices working within another device or devices. Such an arrangement is shown in FIG. 10 in which the introducer device 12 heretofore described is shown being used in connection with a surgical device 81 which is provided with a shaft 82 and a cap 83 having the flexible valve 11 of the present invention incorporated therein. Another device 86 can be introduced through the valve 11 provided in the device 81 and is provided with a shaft 87 and a cap 88 which contains another flexible valve 11. By way of example, the device 86 can be utilized as a fluid introducer. Another device 91 can be introduced through the device 86 and is provided with a shaft 92 which is provided with a connector 93 connected to electrical conductors 94.

Thus, it can be seen by way of example that a plurality of surgical tools can be nested together in such a manner so that one can be inserted through another to go through a common opening as, for example, in the abdominal wall to make it possible to perform a multiplicity of procedures. Also as heretofore described, a plurality of devices can be inserted through a single introducer as, for example, by introducing one tool and then withdrawing the same and thereafter inserting another tool. The flexible valve 11 serves to retain the gas within a cavity while at the same time permitting easy insertion and removal of the tools and forming an excellent seal with the tool in place or with a tool removed. The flexible valve provides two-stage sealing from one sealing around the circumference of the tool when the tool is passing through the valve and another seal when the tool is extracted.

What is claimed is:

1. In a flexible valve adapted to have a device inserted therethrough, a body of elastomeric material comprising a cylindrical wall portion with a bore extending therethrough and having a longitudinal central axis, at least three flexible leaflets adjoining the cylindrical wall portion and extending outwardly therefrom in the direction of the longitudinal central axis, said at least three leaflets subtending 360° of the cylindrical wall portion and being adapted to have said device inserted therethrough and withdrawn therefrom without inversion, each leaflet having inwardly inclined planes adjoining first and second wall portions and being vee-shaped in cross-section in a plane perpendicular to the longitudinal central axis, each of said first and second wall portions having first and second sealing surfaces at their distal extremities, said first and second sealing surfaces of one of said leaflets being adapted to abut the second sealing surface of the adjacent leaflet on one side of said one leaflet and abut the first sealing surface of the adjacent leaflet on the other side of said one leaflet whereby a yieldable seal is formed by the abutting sealing surfaces of the leaflets when a device is not present in the valve.

2. A valve as in claim 1 wherein said first and second sealing surfaces extend in directions substantially parallel to the longitudinal central axis.

3. A valve as in claim 2 wherein said first and second wall portions of each leaflet are provided with planar surfaces which adjoin said sealing surfaces at substantially 90°.

4. A valve as in claim 1 together with seal ring means formed in the body of elastomeric material to engage the tool to form a seal therewith when a tool extends through the valve, said seal ring means having a portion which is substantially semi-circular in cross section to provide a rounded surface engaging the tool.

5. A valve as in claim 1 wherein said body includes an annular flange formed integral with the cylindrical wall portion and extending radially outwardly therefrom.

6. A valve as in claim 1 wherein said leaflets have a wall thickness ranging from 0.020 to 0.040 inches.

7. A valve as in claim 6 wherein said leaflets have a wall thickness of approximately 0.030 inches.

8. A valve as in claim 1 wherein said elastomeric material is a urethane compound.

9. A valve as in claim 1 wherein four leaflets are provided.

10. A valve as in claim 1 wherein three leaflets are provided.

11. A valve as in claim 1 wherein said first and second wall portions have distal extremities which are tapered leading to the first and second sealing surfaces.

12. A valve as in claim 1 wherein each of said leaflets has a single contact with a device when it is inserted through and withdrawn from the valve.

13. In a device adapted to have a tool inserted therethrough, first and second parts, said first and second parts having bores extending therethrough, a flexible valve mounted between said first and second parts and having a longitudinal central axis in alignment with the bores of the first and second parts, and means interconnecting said first and second parts to retain said flexible valve between said first and second parts, said flexible valve having a cylindrical wall portion and at least three flexible leaflets adjoining the cylindrical wall portion and extending outwardly therefrom in the direction of the longitudinal central axis, said at least three leaflets subtending 360° of the cylindrical wall portion and permitting the tool to be inserted and to be withdrawn without inversion.

14. A device as in claim 13 wherein said valve is provided with an annular flange and wherein said means for interconnecting said first and second parts includes means for clamping said flange between said first and second parts.

15. In an assembly, a first device having a cylindrical shaft with a bore extending therethrough, a flexible valve mounted in said first device having at least three leaflets with the leaflets facing in one direction into the bore, a second device having a shaft with a bore extending longitudinally thereof and with the shaft extending through the flexible valve of the first device, a flexible valve mounted in the second device and having at least three leaflets extending into the bore of the second device and facing in the same direction as the leaflets of the flexible valve in the first device said flexible valve of each of said first device and said second device comprising a body of elastomeric material having a cylindrical wall portion with a bore extending therethrough and having a longitudinal central axis, at least three flexible leaflets adjoining the cylindrical wall portion and extending outwardly therefrom in the direction of the longitudinal central axis, said at least three leaflets subtending 360° of the cylindrical wall portion and being adapted to have said device inserted therethrough and withdrawn therefrom without inversion, each leaflet having inwardly inclined planes adjoining first and second wall portions and being vee-shaped in cross-section in a plane perpendicular to the longitudinal central axis, each of said first and second wall portions having first and second sealing surfaces at their distal extremities.

16. An assembly as in claim 15 together with a third device having a shaft extending through the flexible valve of the second device and flexible valve means mounted within the third device and having at least three leaflets extending into the bore of the third device in the same direction as the leaflets of the flexible valve in the second device.

* * * * *